United States Patent [19]

Mouney

[11] Patent Number: 5,183,467
[45] Date of Patent: Feb. 2, 1993

[54] NASAL ASPIRATOR

[76] Inventor: Daniel F. Mouney, 1616 Lakeshore Dr., New Orleans, La. 70122

[21] Appl. No.: 517,577

[22] Filed: May 1, 1990

[51] Int. Cl.$^5$ .................... A61M 37/00; A61M 1/00; A62B 00/00
[52] U.S. Cl. .................... 604/149; 604/315; 128/205.19
[58] Field of Search .................... 604/140, 149, 94, 313, 604/315, 131, 133, 54, 73, 94, 131, 147, 181, 30; 128/205.19; 251/353, 354

[56] References Cited

U.S. PATENT DOCUMENTS

| | | | |
|---|---|---|---|
| 3,348,742 | 10/1967 | Assalit | 251/354 |
| 3,774,613 | 11/1973 | Woods, Jr. et al. | 604/149 |
| 4,888,003 | 12/1989 | Johnson et al. | 604/320 |

FOREIGN PATENT DOCUMENTS

| | | | |
|---|---|---|---|
| 0278689 | 8/1988 | European Pat. Off. | 604/30 |
| 1109970 | 9/1957 | Fed. Rep. of Germany | 251/354 |

Primary Examiner—Randall L. Green
Assistant Examiner—R. Clarke
Attorney, Agent, or Firm—Keaty & Keaty

[57] ABSTRACT

The invention relates to a nasal aspirator which is used to dislodge and remove secretions, mucus and debris from a nasal passageway of the user. The device is provided with a housing, one end of which is adapted for mounting on a faucet of a liquid fluid source. The second end of the housing serves as an outlet of the device. A vacuum container is in fluid communication with the housing in such a way that opening of a fluid source through the housing causes creation of at least partial vacuum within the container. A nasal valve is in fluid communication with the housing and the vacuum container. The nasal valve includes a nasal seal, one end of which is positioned in the nasal passageway and which is carried by a tube, the second end of which unseats the valve element of the nasal valve to open the fluid communication between the nasal passageway and the housing. The rapid manual opening of the nasal valve causes creation of an impulse, or explosive shock which dislodges secretions from the nasal passageway and moves them towards the outlet of the housing. Continuous water flow through the housing insures continuous application of a suction force until such time as the nasal passageway is secretion-free.

8 Claims, 1 Drawing Sheet

NASAL ASPIRATOR

BACKGROUND OF THE INVENTION

This invention relates to a device for the aspiration and removal of fluids from the body. More specifically this invention relates to an aspirator for removing mucus, debris, secretions and the like from the nasal sinus area.

Many individuals are afflicted with sinus conditions which result in congestion of the nasal and sinus areas. This excessive build-up of mucus, debris, secretions and the like causes considerable discomfort to these unfortunate individuals.

At times, such as in the instance of a patient with a tracheal disorder or in case of an inexperienced small child, these individuals are not able to clear this build-up from the nasal and sinus passageways and have to undergo a great amount of discomfort.

In these instances it is necessary to provide some assistance to these individuals in order to remove the secretion and build-up.

There are many devices which address the general problem of clearing fluids, debris, mucus, secretions and the like from the nasal and sinus passages. See U.S. Pat. Nos. 3,833,001; 2,900,978; 2,245,653; 1,025,504; 1,893,724; 3,761,996; 1,910,935; and 3,774,613.

The major drawback to these previous designs revolves around the fact that these devices are used on loose or free flowing matters and do not anticipate any blockage or heavy congestion. There is a variation on the aspirators which provide some pre-determined vacuum pressure for removing fluids, debris and the like.

It is suggested that in the instances of heavy congestion, the vacuum pressure is merely increased until the material to be aspirated is loosened for convenient extraction. This poses unnecessary constant pressure on vital soft tissue organs which may prove damaging.

The present invention contemplates provision of a nasal aspirator which enables a person to clear ones nasal an/or sinus passages without the direct supervision of doctors or nurses by providing a continuous suction of the secretion/debris which is preceded by a pressure impact to dislodge any build-up or blockage.

SUMMARY OF THE INVENTION

The present invention overcomes the shortcomings of the prior art and achieves its objects in a simple and straight forward manner.

The nasal aspirator is provided with a vacuum creation means which is adapted for connection to a liquid flow source, such as a faucet at one of its sides, having a second, outlet side, open. A flow control means such as a venturi is mounted inside said vacuum creation means in order to control the flow of fluid from the faucet to the outlet. The nasal aspirator further comprises a vacuum container means, such as plastic or glass bottle of sufficient volume to create a shock impulse when the nasal valve is open. The nasal valve means comprises a valve element which is held in a closed position by a tension spring and is opened manually by compressing on an elongated tube, one end of which is positioned in the user's nasal passageway.

A vacuum container, such as a plastic or glass jar, having a sealed tubing extending through the throat of the jar allows communication between the vacuum creation means, the vacuum container and the nasal valve means. Once the faucet is opened, the air is sucked through the side arm from the vacuum container to create at least partial vacuum therein. Once such vacuum is reached, the valve is manually opened, by depressing the end of the tubing and moving the valve element from its seated position against the strength of the tension spring. A rapid influx of air causes an impulse shock, withdrawing secretions from the nasal passageway and drawing them into the vacuum creation means, to the outlet thereof. A continuous flow of liquid through the vacuum creation means insures a continuous suction force applied on the outlet end of the tube positioned in the nasal passageway until such time as substantial all secretions are removed.

It is therefore an object of the present invention to provide a nasal aspirator device for the removal of fluids, mucus, debris, secretion and the like, from the nasal passageways of a user.

It is a further object of the present invention to provide an inexpensive, easy to use nasal aspirator.

It is still a further object of the present invention to provide a method for removing secretions from nasal passageways of the user.

It is still a further object of the present invention to provide a method of removing secretions from the nasal passageway comprising the step of creating an impulse shock for initial dislodging of the secretions in the nasal passageways.

These and other objects of the present invention will be apparent to those skilled in the art from the following description of the invention.

DETAILED DESCRIPTION OF THE PREFERRED EMBODIMENT

Figure 1:
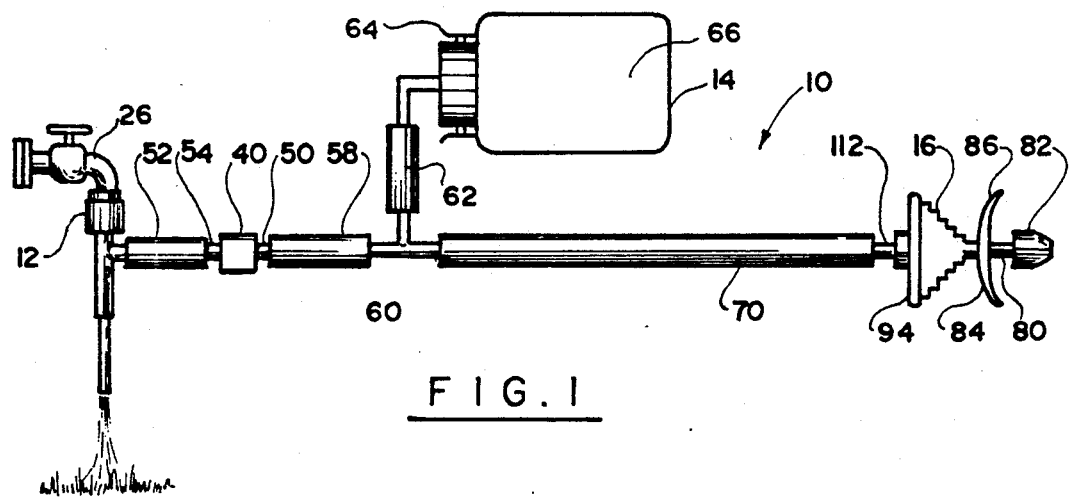
FIG. 1 is a full schematic view of the device of the present invention connected to a water faucet.
Figure 4:
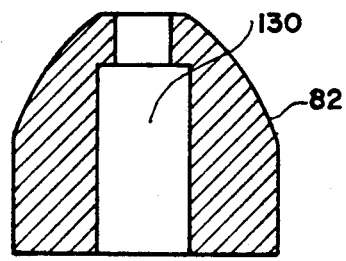
FIG. 4 is a sectional view of the nasal seal of the nasal valve means.

Referring now to the drawings in detail, numeral 10 designates the nasal aspirator device in accordance with the present invention. As shown in FIG. 1, the device 10 comprises a vacuum creation means 12, a container 14 and a hand operated nasal valve means 16, all of the elements of the device 10 being connected by a number of conduits, as will be described below.

Figure 2:
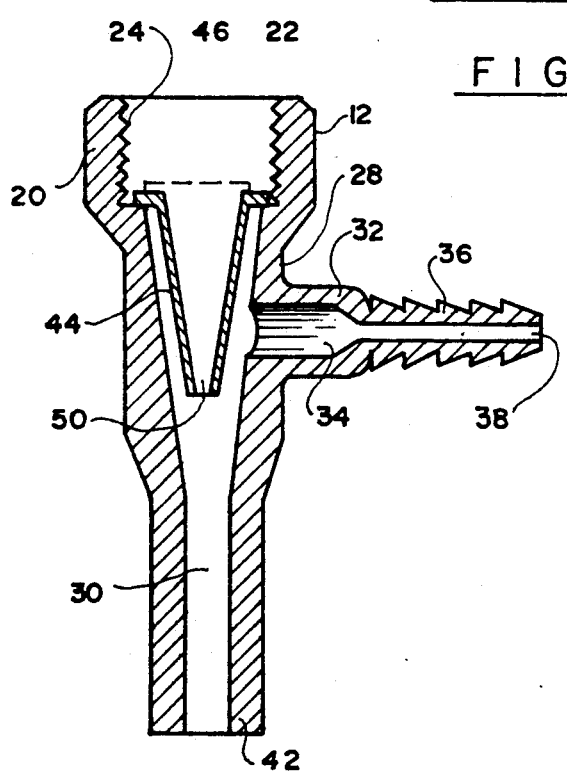
FIG. 2 is a cross-sectional view of the vacuum creation means for the device of the present invention.

Referring now to FIG. 2, which shows a detailed cross-sectional view of the vacuum creation means 12, the means are shown to comprise a tubular collar 20 having an interior opening 22 formed by interior threaded wall 24. The threads extend through substantially the entire length of the annular wall 24 and are adapted for matching engagement with exterior threads of a conventional faucet 26 in a manner schematically illustrated in FIG. 1.

The vacuum creation means 12 further comprises an elongated housing 28 which has an interior central opening 30 extending through substantially the entire length thereof, and which is in fluid communication with the opening 22 of the collar 20.

A side arm 32 having an interior central opening 34 intercepts at a right angle the central opening or passageway 30, with which it is in fluid communication. The side arm 32 has external threads 36 extending from the outer-most end 38 of side arm 32 a distance towards the point of attachment of the side arm 32 to the housing 28. As will be explained below, the side arm is adapted for engagement through a tubing element with a check valve means 40 which is mounted in fluid communication with a conduit connecting the vacuum creation means 12 with the pump means 16. The check valve means 40 maintains vacuum created by the vacuum creation means 12 at a maximum level.

The lowermost end of the elongated housing 28 forms an open end 42 which serves as a liquid outlet of the device 10.

Mounted within the body 28 is a flow control means 44 which in the embodiment shown in FIG. 2 is a venturi having a throat opening 46 adjacent the uppermost end of the housing 28, which, in turn, is at the approximately same level as the lower part of the collar 20. The restricted size passageway 50 which is formed by the lowermost portion of the venturi 44 is positioned at a level below the line of intersection between the passageway 34 and the passageway 30. The exterior wall of the venturi 44 is smaller in diameter than the diameter of the passageway 30, thus allowing fluid communication between the passageway 34 and passageway 30, without undue restriction of the passageway 34.

A flexible tubing element 52 fits over the threads 36 at one of its ends and fits over an inlet tubing 54 of the check valve means 40. The outlet conduit 56 of the check valve means 40 is connected by a flexible tubing 58 to a T-shaped connector 60, the vertical leg of which is fluidly connected to a tubing 62. The tubing 62 serves as a fluid inlet line of the vacuum container means 14. The fluid inlet conduit 62 sealingly engages a throat 64 of the vacuum container means 14, such that the inlet tubing 62 is in fluid communication with an interior chamber 66 formed by the container means 14. The horizontal portion of the T-connector 60 is joined with a flexible tubing 70 and is in direct line of communication with the nasal valve pump means 16.

Figure 3:
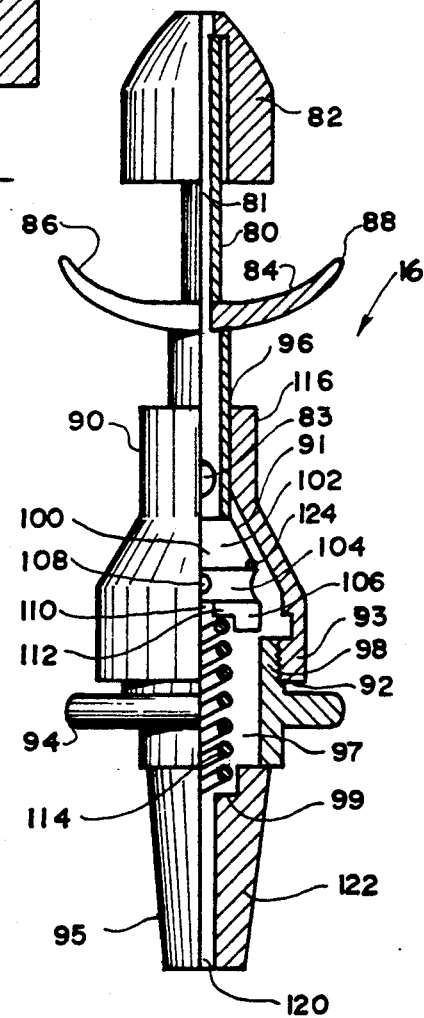
FIG. 3 is a cross-sectional view of the hand-operated nasal valve means of the device of the present invention in an open position.

Reference will now be made to FIG. 3, showing a cross-sectional view of the hand operated valve means 16. As can be seen in the drawing, the valve means 16 comprises an elongated resilient tubing 80 having a central conduit 81 therein and carrying at its uppermost end a nasal plug 82 which is fitted on the tip of the tube 80. The plug 82 has an internal opening 130 of a diameter substantially equal to, or slightly greater than the exterior diameter of tube 80, so as to frictionally engage the tube 80. One or more transverse aperture 83 is formed through the wall of the tube 80, the aperture 83 allowing fluid communication between the conduit 81 and chamber 91 of a housing 90, as will be addressed below.

Frictionally mounted on the tube 80 a distance inwardly from the plug 82 is a handle means 84 which fits over the tubing 80 (or can be integrally formed with tubing 80) and which has a pair of finger plates 86 and 88 extending outwardly from a central portion of the handle means 84. The finger plates 86 and 88 are made as upwardly curved plates that are conveniently shaped to be engaged by fingers of the user, as will be described in more detail hereinafter.

As can be seen in FIG. 3, a portion of the tubing 80 extends below the handle means 84 and is circumferentially surrounded by a bell-shaped housing 90 which is hollow on the interior and forms an open interior chamber 91. The bottommost edge 92 of the bell-shaped housing, when assembled is adjacent to an enlarged diameter circular support plate 94 which forms a part of a support means 95.

The support means 95 further comprises an externally threaded portion 98 which extends vertically upwardly from an upper surface of the support plate 94 and threadably engages with matchingly internally threaded portion 93 of the housing 90.

The valve means 16 further comprises a valve element 100 which has an upper frustoconically shaped portion 102, the widest portion of which has a diameter greater than the diameter of the central opening 96 formed in the upper part of the housing 90, but smaller than the diameter of the remainder of the chamber 91.

The valve element 100 further has a middle portion 104 of a reduced diameter and a lower cylindrical portion 106 which diameter is substantially equal to the diameter of the widest part of the portion 102. The exterior diameter of the cylindrical portion 106 is slightly smaller than the interior diameter of the central interior chamber 97 of the support means 95. The upper portion 102 is formed solid, and a plurality of radial openings 108 are formed in the middle portion 104. The lower portion 106 has an axial opening 110 which is in fluid communication with the radial openings 108 and exterior of the valve element 100. An internal shoulder 112 is formed in the support means 95 below the support plate 94. The shoulder 112 faces downwardly, while the shoulder 99 faces upwardly.

A compressible tension spring 114 urges at its uppermost end against the shoulder 112. The lowermost portion of the tension spring 114 urges against a top surface of the shoulder 99 inside the support means 95. When the valve means 16 is in a closed position, the spring 114 forces the valve element 100 upwardly, obstructing and closing internal central opening 96 extending through the housing 90. The portion 102 frictionally engages the walls of the part 116, and when depressed by the lower end of the tube 80, moves from the smaller diameter part 116 downwardly into a greater diameter chamber 91, thus opening a fluid passageway from the tube 80 into the member 100 and from then on into a central opening 120 formed in the lower end of the support means 95.

Fixedly attached to the support plate 94 and extending downwardly from the bottom surface thereof is an outlet conduit 122 which is connected to a flexible conduit 70. The fluidly sealed connections between respective flexible conduits and tubings are made in conventional manner, which is well within the knowledge of those skilled in the art.

The size of the plug 82 is such as to fit within a nasal passage of an adult or child while preventing the user from extending the tube 82 a distance within the nasal passageway to cause damage to the soft tissue forming the nasal passageway. The optional advantage afforded by the plug, or seal 82 is creation of a seal in the nasal passageway, opening only the tip of tube 80 for fluid communication with the nasal passageway of the user.

In operation, the vacuum creation means 12 is connected to a faucet 26 by attaching a collar 20 to a faucet. A flow of water is initiated through the interior of the vacuum creation means 12, exiting through a restricted orifice 50 of the venturi 44.

A vacuum is created in the side arm passageway 34 and thus, in the vacuum reservoir container 14. The normally closed valve means 16 is positioned in such a manner that the seal or plug 82 is within the nasal passageway of the user. The vacuum created in the chamber 66 of the container 14 is maintained at its maximum level by the check valve means 40. The device 10 is activated by compressing the handle means 84, moving the tube 80 downwardly into the housing 90.

The lowermost end of the tube 80 depresses the top of the portion 112, unseating it and moving it downwardly against the tension of the spring 114. A fluid passageway is rapidly opened between the nasal passage of the user, the opening 93 and the interior of the axial opening 110 through the radial ports 108. The air flow exits the opening 93, is admitted into chamber 91 and is drawn into radial ports 108. The flow then enters the axial opening 110 and exits into the chamber XX from where it leaves through the fluid outlet means 122, carrying dislodged secretions. The valve means 16 which is normally closed, rapidly opens communication with the interior chamber 66 of the container 14 causing a shock-like impulse, drawing secretions and debris from the nostril of the user.

The airflow is continued to enter the nasal passageway until the pressure on the valve means side of the device 10 is substantially equalized, by the depletion of the vacuum in chamber 66, with a side of the device 10 occupied by the vacuum creation means 12. A continuous airflow will cause further secretion, mucus and debris to dislodge and draw them into the conduit 70, into the side arm 32 and out of the device 10 through the outlet side 42 of the vacuum creation means 12.

Suction force created by the water flow passing through the vacuum creation means is received in the side arm 32 and is transmitted to the tube 80, continuing to withdraw secretions from the nasal passageway until the water flow is interrupted.

The force of the impulse can be easily regulated by changing the dimension of the chamber 66 of the container 14. For example, it can be accomplished by filling the container with water and by varying the length of tubing connecting the elements of the device of the present invention.

The rate of the continuous flow, which follows the initial shock impulse depends on the rate of water flow through the faucet 26 and consequentially, through the vacuum creation means 12.

As a result, the nasal passageway of the user is cleared, giving relief to the person from nasal congestion or, if used for cleaning, for dislodging extraneous matter from the nasal passage.

The device of the present invention closely imitates human reflexes which cause removal of foreign matter, secretions and the like from the respiratory tract. A sneeze or cough begins with a deep inspiration and is followed by a forced expiration against a closed glottis. It was found that intrapleural pressure may reach 100 mmHg during this phase. The glottis opens suddenly and pressure in the air ways falls rapidly, creating an explosive expiration. The high rate airflows carry the irritant, some mucus and the like, out of the respiratory tract through the nose or mouth.

The device 10 also creates such explosive pressure build up and rapid release as to imitate the natural reflex.

A number of fluid seals can be mounted within the device 10, such as 0-ring 124 mounted on the portion 102, so as to prevent leakage of fluid between the sealed parts of the device 10.

The connecting tubing and conduits of the present invention can be made from elastomeric material, such as plastic, which is flexible and easy to clean. The tube 80 is fully detachable from the bell-shaped housing 90, permitting thorough cleaning of the tube and plug 82 by running water or with suitable detergent.

All connections between the flexible tubes and conduits are easily dismantled, so as to permit cleaning of individual elements forming the device of the present invention.

Many changes and modifications can be made within the design of the present invention without departing from the spirit of the present invention. I, therefore, pray that my rights to the present invention be limited only by the scope of the appended claims.

I claim:

1. A method for removing secretions from a nasal passageway, the method comprising the following steps:

providing a vacuum creation means having an inlet side and an outlet side, said vacuum creation means comprising an elongated housing having an upper internally threaded collar for engagement with a liquid flow source, and elongated housing with a central internal opening, a flow control means mounted in said central opening and a side arm integrally connected to said housing and extending outwardly therefrom, said side arm being formed with an internal passageway in fluid communication with the central opening;

providing a nasal valve means connected in fluid communication to said vacuum creation means, said nasal valve means comprising an elongated tube having a first end and a second end, a nasal seal means carried by the first end of the tube, a handle means attached to the tube a distance from said nasal seal means and a normally closed nasal valve means mounted within said housing and movable between a first, closed position substantially sealing communication between said second end of the tube and exterior of the nasal valve means and a second, opened position allowing fluid communication between the exterior of the nasal valve means and the second end of the tube;

providing a vacuum container means mounted between said vacuum creation means and said nasal valve means;

connecting an inlet side of said vacuum creation means to a liquid flow source;

positioning the nasal seal means within the nasal passageway of the user, such that the nasal seal means seals the nasal passageway;

initiating a flow of liquid through said vacuum creation means, withdrawing air from said vacuum container means to create at least a partial vacuum within said vacuum creation means;

opening said nasal valve means and creating an impulse shock for withdrawing secretions from the nasal passageway and directing them from the nasal valve means to the outlet side of the vacuum creation means; and continuing a flow of liquid through said vacuum creation means until such time as the nasal passageway is substantially secretion-free.

2. The method of claim 1, further comprising the step of providing a check valve means for maintaining a vacuum created by said vacuum creation means at a maximum level.

3. The method of claim 2, wherein said nasal valve means further comprises a bell-shaped hollow housing receiving the second end of the tube in frictional engagement with an upper portion of the housing, a support means having an exteriorly threaded upper portion which threadably engages an interiorly threaded lower portion of the housing, said support means having an interior chamber and a lower part which is provided with a central opening, and wherein said valve element is mounted within said housing.

4. The method of claim 3, wherein said valve element comprises an upper frustoconically-shaped portion, a reduced diameter middle portion and a lower cylindrical portion, said middle portion being provided with a plurality of radial ports, said lower portion being provided with an axial opening extending through the lower portion and fluidly communicating with said radial ports and an internal chamber formed by said bell-shaped housing.

5. The method of claim 4, wherein said lower portion of the valve element is provided with a downwardly facing internal shoulder and said lower part of the support means is provided with an upwardly facing internal shoulder.

6. The method of claim 5, wherein the second end of the elongated tube is provided with at least one transverse opening in fluid communication with a central opening of the tube and exterior of the tube.

7. The method of claim 6, wherein said nasal valve means further comprises a tension spring means which urges with its first end against said shoulder of the valve element which urges against the shoulder of the support means, said spring means being compressed under the force exerted by said elongated tube.

8. The method of claim 7, wherein said tension spring means retains said nasal valve means in the first closed position.

* * * * *